United States Patent [19]

Sherman

[11] Patent Number: 4,560,491

[45] Date of Patent: Dec. 24, 1985

[54] SOFT CONTACT LENS WETTING SOLUTION AND IN-EYE COMFORT SOLUTION CONTAINING PRESERVATIVE AND METHOD

[75] Inventor: Guy J. Sherman, Mandeville, La.

[73] Assignee: Sherman Laboratories, Inc., Abita Springs, La.

[21] Appl. No.: 641,996

[22] Filed: Aug. 20, 1984

Related U.S. Application Data

[63] Continuation-in-part of Ser. No. 537,245, Sep. 28, 1983, Pat. No. 4,529,535, which is a continuation-in-part of Ser. No. 384,110, Jun. 1, 1982, abandoned.

[51] Int. Cl.$^4$ ................................................ C11D 3/48
[52] U.S. Cl. .................................... 252/106; 252/173; 252/174.23; 252/174.24; 252/351; 252/DIG. 2; 252/DIG. 14; 422/28
[58] Field of Search ................... 252/106, 173, 174.23, 252/174.24, DIG. 14, 351; 424/78, 80, 251; 514/275; 422/28

[56] References Cited

U.S. PATENT DOCUMENTS

| | | | |
|---|---|---|---|
| 3,549,747 | 12/1970 | Krezanoski et al. | 424/78 |
| 3,639,576 | 2/1972 | Kaspar et al. | 424/78 |
| 3,954,965 | 5/1976 | Boghosian et al. | 424/81 |
| 4,287,175 | 9/1981 | Katz | 424/78 |
| 4,470,978 | 9/1984 | Stolar | 424/229 |

OTHER PUBLICATIONS

The Merck Index, An Encyclopedia of Chemicals & Drugs, Merck & Co., N.J. Ninth Ed., 1976, p. 1246

*Primary Examiner*—Prince E. Willis
*Attorney, Agent, or Firm*—Jenner & Block

[57] ABSTRACT

Aqueous compositions for the wetting and rewetting of contact lenses and especially silicone, silicone copolymer (gas-permeable) and soft contact lenses are provided that include a preservative system. The preservative system includes trimethoprim, and benzyl alcohol as an adjuvant bactericide and optionally a salt of EDTA. The use of preservatives which are known to cause eye irritation and lens discoloration such as thimerosal, sorbic acid, potassium chloride and chlorhexidine is eliminated. Wetting and re-wetting compositions which incorporate the preservative system and include thickening and wetting agents are also provided. The wetting and re-wetting solutions can be instilled directly into the eye during contact lens wearing periods and are especially useful for wetting silicone, silicone copolymer and soft daily and extended wear contact lenses.

19 Claims, No Drawings

SOFT CONTACT LENS WETTING SOLUTION AND IN-EYE COMFORT SOLUTION CONTAINING PRESERVATIVE AND METHOD

RELATED APPLICATION

This application is a continuation-in-part application of U.S. patent application Ser. No. 537,245, filed Sept. 28, 1983, now U.S. Pat. No. 4,529,535, which is a continuation-in-part application of U.S. patent application Ser. No. 384,110, filed June 1, 1982, now abandoned.

BACKGROUND OF THE INVENTION

Just as there are marked differences in the structure and composition of hard contact lenses, cellulose acetate butyrate (CAB) and silicone copolymer gas-permeable contact lenses and soft contact lenses, there are also marked differences in the maintenance and care or treatment with the various types of hard, CAB, silicone and soft lenses. While patient care and treatment of hard contact or conventional contact lenses is relatively simple and uncomplicated, the proper care and treatment of CAB and silicone copolymer lenses (gas-permeable) and the newer soft and hydrophilic lenses has proved to be more complex, time consuming and costly to the patient.

The primary difference between the conventional hard contact lens and the silicone copolymer lenses and the more complex soft lenses is the hydrophobic nature of the silicone copolymer lenses and the marked increase in the polar or water attracting centers of the hydrophilic gel material from which the soft contact lenses are made. It is this property of the hydrophilic gel lens that gives the soft lens its own unique physical properties and clinical behavior. This polar or water attracting center of the gel material is represented in the hydroxyethyl methacrylate bond as a hydroxyl group (—OH) which attracts and holds large amounts of water. It is this high water content held in the expanded matrix of the hydrophilic gel lens which leads to the special difficulties in cleaning and disinfecting or asepticising the soft hydrophilic lens. The hydrophilic nature of soft contact lenses makes the lenses vulnerable to bacterial contamination. While studies have demonstrated that bacteria cannot penetrate the actual intromolecular pores of the hydrophilic lens, except in defective lenses, the bacteria have an affinity for protein and tear deposits on the surfaces of the lens matrix. In particular, the tears and fluids absorbed by the soft lenses serve as excellent bacterial culture media. If defects or nicks occur in the lenses either during manufacture or subsequent patient wear, bacteria may find a haven to grow and be sheltered from superficial lens cleaning and disinfection.

Potentially harmful fungi are also a possible danger to the soft contact lens. Fungi, like bacteria, can thrive in tear secretions, other fluids or deposits and penetrate the lens material directly if enzymatic degradation of the lens material has taken place.

Similarly, any substantial residual proteinaceous or tear secretion deposits or lipid deposits remaining in or on the lens may readily overwhelm and inactivate the most effective germicidal components of a disinfecting system, and may thus serve to act as a growth media for a variety of potentially harmful microorganisms and fungi. Therefore, it is important that prior to storing the soft contact lenses in a disinfecting solution, protein and lipid deposits be removed from the lens surfaces so that the disinfectant properties of the sterilizing solution or method will not be overwhelmed by gross organic or inorganic deposits and pollutants. Therefore, an effective cleaning step or steps is an essential and mandatory part of any effective soft lens treatment and maintenance regimen.

Wetting solutions are used to prepare the contact lenses prior to insertion into the eye and are known in the prior art. Prior art contact lens wetting solutions have primarily involved the use of polyvinyl alcohol as a wetting agent and methyl cellulose or hydroxyethyl cellulose as viscosity building agent. These prior art solutions have also contained sufficient amounts of water-soluble salts, generally sodium chloride, to make them isotonic or hypertonic with human serum and tear fluid. For example, hypertonic wetting solutions are disclosed in U.S. Pat. No. 3,549,747.

Re-wetting solutions are instilled directly into the eyes when contact lenses are being worn. Such solutions can also be used before or after wearing periods. The purpose of re-wetting solutions include providing comfort and relubrication for the eye.

Because of the potential for bacterial contamination, wetting and re-wetting solutions generally include a preservative system to prevent or inhibit microbial growth, especially where multi-dose containers of the solution are prepared. Generally, where no preservative is employed, single dose containers are utilized, which result in greater expense.

Preservative systems known in the prior art for wetting solutions are disclosed in U.S. Pat. No. 3,549,747. Known preservatives include benzalkonium chloride, thimerosal, chlorhexidine, sorbic acid and potassium sorbate. However, these compounds have drawbacks in that they can be concentrated in the lens matrix and cause irritation, excessive burning, red eye and lens discoloration, which can prevent the patient from wearing the lenses or can otherwise be hypersensitive and annoying to the eye.

With the advent of extended wear contact lenses, it becomes even more important to avoid such problems, since those lenses can remain in the eye for several weeks. Thus, a need has arisen for an effective preservative system which avoids the use of preservatives known to cause eye irritation and lens discoloration and which is suitable for soft contact lenses in a wetting and rewetting solution. A need also exists for a soft contact lens wetting and re-wetting solution which incorporates such a preservative system. Finally, a need exists for an "in-eye" re-wetting solution that can be instilled directly into the eyes to provide re-lubrication and comfort for the eyes having such a preservative system.

SUMMARY OF THE INVENTION

This invention relates to novel and effective silicone copolymer (gas-permeable) contact lens and soft contact lens preservative systems and wetting and rewetting solutions. More particularly, this invention relates to highly effective silicone copolymer and soft contact lens wetting and re-wetting solutions that can be applied directly into the eye that includes a preservative system which avoids hypersensitivity and lens discoloration problems associated with preservative systems containing thimerosal, sorbic acid, potassium chloride or chlorhexidine, for example. The invention is especially suitable for use with silicone, silicone copolymers and soft lenses (such as HEMA contact lenses, for example) including extended wear contact lenses, and reference to hard lenses includes silcone, silicone copolymers and extended wear lenses. The invention is also suitable for use in connection with hard contact lenses. In fact, the wetting and re-wetting solution can be used directly in the eye by persons who do not wear contact lenses, such as for relief of dry eye syndromes, idiopathic ocular discomfort and other conditions. As used hereinafter and in the claims, the term "wetting solution" or "wetting composition" includes re-wetting solutions or compositions that are suitable for application directly into the eye.

In another aspect, this invention relates to a soft contact lens wetting and re-wetting composition that effectively wets the surface of contact lenses, especially soft and extended wear lenses. The solution is also useful as an in-eye comfort solution during and after contact lens wearing periods. The solution can also be used as an in-eye comfort solution whether or not contact lenses are worn.

In accordance with the invention, a preservative system is provided that is incorporated in a contact lens wetting and/or re-wetting solution. The preservative system is effective for maintaining the solution sterile, preventing bacteria and other organisms from contaminating the solution after its container has been opened and an initial use has been made of a portion of the solution, for example. While intended primarily for use in connection with soft contact lenses, including extended wear lenses, the preservative system may also be used with hard contact lenses.

The preservative system of the invention is safe and effective, is not deleterious to the human eye or ocular tissue, and when present in a wetting solution, can be instilled directly into the eye. Further, the preservative system does not discolor soft contact lenses and is not otherwise deleterious to soft lenses. Accordingly, the shortcomings of preservative systems containing compounds such as thimerosal, sorbic acid, potassium chloride or chlorhexidine, for example, are avoided.

The preservative system of the invention for use in a contact lens wetting composition which can be instilled into the eye includes an effective amount of trimethoprim and at least one adjuvant bactericide comprising benzyl alcohol for maintaining the sterility of the composition. The composition optionally includes ethylenediamine tetraacetic acid (EDTA) or a water soluble salt thereof. Generally, the amount of trimethoprim is from about 0.05% to about 2.0%, the amount of benzyl alcohol is from about 0.1% to about 5.0% and the amount of EDTA is from about 0.025% to about 0.5%, all by weight of the total composition. In addition to acting as an adjuvant bactericide, the benzyl alcohol functions as an aid in dissolving the trimethoprim which is present in the composition.

In accordance with another aspect of the present invention, a method is provided for maintaining the sterility of contact lens wetting compositions which method includes providing in the compositions a preservative system in accordance with the invention. The sterility of the composition is preserved while avoiding the use of bactericides which are absorbed by soft lenses and which are incompatible with ocular tissue or otherwise cause eye irritation and/or lens discoloration.

In accordance with the preferred aspects of the present invention, a composition suitable for wetting and re-wetting contact lenses is provided.

The wetting composition includes a preservative system and a wetting system. Preferably, the aqueous wetting composition according to the invention that includes a wetting system and a preservative system has a tonicity of from about 1.00 to about 1.45 and a pH of from about 7.0 to about 8.0 and a viscosity of from about 26 to 40 cps.

In accordance with one embodiment of the invention, an aqueous wetting composition is provided that is especially suitable for wetting soft contact lenses. The wetting composition contains a preservative system of the above description and a wetting component or components. Any suitable wetting component may be utilized that is suitable for wetting contact lenses. If the wetting composition is intended for wetting soft contact lenses, then the wetting component should be suitable for use with soft contact lenses.

Generally, the wetting system should be completely miscible with water at the utilized concentrations and generally should also provide a clear solution. In addition, the wetting system must not act adversely with the type of contact lens with which use is intended, nor with other materials present in the solution and, finally, must not irritate the eye.

The wetting system includes at least one component suitable wetting contact lenses. Usually, the wetting system will include a viscosity-building agent and a wetting agent suitable for soft contact lenses. Suitable viscosity-building agents include water soluble cellulosic polymers, which may be synthetic or natural, for example. Such materials also assist in wetting the lenses. Suitable wetting agents include polyvinyl alcohol and polyvinylpyrrolidone and mixtures thereof, for example. Other suitable viscosity-building agents and wetting agents for contact lens wetting solutions will be known to those skilled in the art.

Suitable cellulosic polymers include hydroxyethylcellulose, methylcellulose, carboxymethylcellulose, natural gums and mixtures thereof. Usually, the amount of cellulosic polymer present in the composition is from about 0.05% to about 0.80% by weight of the total composition.

Usually, the wetting composition will have a viscosity of about 26 to 40 cps at 25° C. Medium grade cellulosic polymers are useful for achieving the desired viscosity.

Preferably, the polyvinyl alcohol utilized is fully hydrolized. Generally, the amount of polyvinyl alcohol present in the composition is from about 0.5% to about 2.5% by weight of the total composition.

Preferably, an additional wetting compound, a polyvinylpyrrolidone polymer, will be utilized, usually in an amount of from about 0.5% to about 2.0% by weight of the total composition.

It is to be understood that the invention is not limited to the foregoing types of wetting agents and viscosity-building agents. Any type of material which can be used to provide the desired wetting action and which is compatible with the preservative system of the present invention and is otherwise suitable for use in a wetting solution or a contact lens wetting solution can be utilized.

Compositions in accordance with the invention have a pH of preferably from about 7.0 to about 8.0. Sodium bicarbonate may be present in the composition, generally from about 0.05% to about 3.0% by weight of the total composition for adjustment of pH.

The soft contact lens wetting or in-eye comfort drop composition according to the invention preferably will have a tonicity of from about 1.00 to about 1.45. Thus, the compositions of the invention are mildly hypertonic to help prevent possible absorption into the lens matrix of foreign matter, bacteria or other residue which could build up and cause contamination problems and deterioration and discoloration of the lens itself. The remainder of the composition is purified water U.S.P.

The wetting compositions of the invention containing polyvinyl alcohol, polyvinylpyrrolidone and/or a cellulosic polymer of the type described are especially useful for wetting silicone copolymer contact lenses after the lenses have been cleaned with a nonionic detergent cleaner suitable for cleaning the lenses such as a cleaner of the type disclosed in U.S. patent application Ser. No. 384,110, filed June 1, 1982, which is hereby incorporated by reference.

It has been discovered that the surface charge or static electricity charge which may be present on silicone copolymer lenses is eliminated or neutralized by such nonionic detergents and makes the lenses wettable by the aforesaid wetting compositions. Failure to eliminate or neutralize such charges can prevent such lenses from being adequately wetted.

Thus, in accordance with another aspect of the present invention, a method of wetting a silicone copolymer contact lens having a surface charge is provided that comprises neutralizing or eliminating the surface charge and contacting the lens with a wetting composition containing at least one wetting component selected from polyvinyl alcohol, polyvinylpyrrolidone and a cellulosic polymer. Suitable wetting components are as previously described herein. One procedure by which the surface charge can be neutralized or eliminated is by contact with nonionic detergent material as aforesaid. The nonionic detergent material is then rinsed from the lens prior to wetting. Suitable nonionic detergents include the hydroxyalkylated and polyoxyalkylated surfactants as described in U.S. patent application Ser. No. 384,110. The preferred non-ionic detergents are a combination of a polyoxypropylene-polyoxyethylene block copolymer, an amphoteric surface active agent and an alkylaryl polyether alcohol as described in U.S. Ser. No. 384,110. Reference is also made thereto for the concentrations of the surfactants and other components which may be present in the cleaner composition.

DETAILED DESCRIPTION OF THE INVENTION

According to the invention, the preservative system, which provides antibacterial and antifungal activity, usually includes from about 0.01% to about 2.0% trimethoprim, preferably about 0.025% by weight of the total composition and benzyl alcohol, usually present in an amount of from about 0.1% to about 5.0% by weight of the total composition. Trimethoprim is also known as 2,4-Diamino-5-(3,4,5-trimethoxybenzyl)-pyrimidine and as Syraprim. See, for example, *The Merck Index*, tenth edition, pg 1,387.

Other adjuvant bactericides may be present in the preservative system, such as, for example, from about 0.025% to about 0.5%, preferably 0.1%, by weight of the total composition of ethylenediaminetetraacetic acid or a water soluble salt thereof which has bactericidal properties. The types of bacteria and other organisms to which the solutions are susceptible to exposure and which are necessary to protect against are adequately rendered inactive or killed by the trimethoprim benzyl alcohol and salts of EDTA.

The inclusion of ethylenediaminetetraacetic acid or a water soluble salt of ethylenediaminetetraacetic acid serves as a buffering and preservative component of the composition according to the invention, and has also been demonstrated to have antibacterial and antifungal properties. The preferred salt of ethylenediaminetetraacetic acid is disodium ethylenediaminetetraacetate (disodium EDTA or disodium edetate). Other salts of EDTA which may be utilized include, for example, mono-, di-, tri- and tetra-alkali metal salts.

Any suitable wetting system can be used in accordance with the invention. The preferred wetting system contains a wetting agent and a viscosity-building agent. An especially preferred wetting system contains hydroxyethylcellulose, polyvinylpyrrolidone and polyvinyl alcohol. A preferred hydroxyethylcellulose is available from Hercules, Inc. of Wilmington, Del. under the trade designation "250 H." A preferred polyvinylpyrrolidone is available from GAF Corporation of New York, New York under the name Plasdone ® C. A preferred polyvinyl alcohol is available from the Monsanto Company of St. Louis, Mo. under the name of "Galvatol" which is partially hydrolized.

The wetting compositions of the present invention are preferably buffered and slightly acid or neutral. The preferred pH range is from about 7.0 to about 8.0. Suitable buffers are known in the art. Suitable buffers include sodium bicarbonate. The preferred combination of buffers is sodium bicarbonate, sodium phosphate (tribasic), sodium biphosphate and sodium bisulfite, in amounts to provide and maintain the desired pH.

The remainder of the wetting composition is purified water U.S.P. and the composition preferably includes combinations of essentially neutral and alkaline salts compatible with ocular tissue and soft contact lens material which are water-soluble, generally present in a concentration to provide an aqueous composition salt content equivalent to from about 1.00 to about 1.45 tonicity. Thus, the soft contact lens cleaning solutions of the present invention can be mildly hypertonic which helps in the prevention of possible absorption into the lens matrix of foreign matter, protein, lipids and bacteria which could build up and cause contamination problems and deterioration and discoloration of the lens itself. Sodium chloride can be present in the soft contact lens wetting composition, usually in an amount from about 0.05% to about 2.0% by weight of the total aqueous composition, for example, and preferably in an amount of about 0.79% by weight of the total aqueous composition. Potassium chloride is another salt which is preferably used in conjunction with sodium chloride and should generally be present in an amount of from about 0.05% to about 2.0% by weight of the total aqueous composition and preferably in an amount of about 0.368% by weight of the total aqueous composition.

| Component | Amount (% by weight) |
| --- | --- |
| Sodium bicarbonate | 0.100 |
| Sodium phosphate (tribasic) | 0.030 |
| Sodium biphosphate | 0.030 |
| Sodium chloride | 0.790 |
| Potassium chloride | 0.368 |
| Disodium EDTA | 0.100 |
| Hydroxyethylcellulose 250H | 0.400 |
| Polyvinyl alcohol | 1.000 |
| Polyvinylpyrrolidone (Plasdone ® C) | 0.500 |

-continued

| Component | Amount (% by weight) |
| --- | --- |
| Trimethoprim | 0.025 |
| Sodium Bisulfite | 0.050 |
| Benzyl Alcohol | 0.200 |
| Propylene Glycol | 0.500 |
| Purified water U.S.P. | Balance to 100 |

While the present invention has been described primarily with respect to wetting solutions, the wetting compositions of the invention containing a water soluble cellulosic polymer, polyvinyl alcohol and polyvinylpyrrolidone and preservative system are especially useful for application directly into the eyes while contact lenses are being worn for effective relubrication and immediate restoration of comfort when applied to eyes which are dry, tight and/or uncomfortable. Such compositions further reduce the tendency of oil and mucous deposits to accumulate on contact lenses. These compositions are especially suitable for use with silicone, silicone copolymer contact lenses and soft contact lenses.

Whereas the present invention has been described with respect to specific embodiments thereof, it will be understood that various changes and modifications will be suggested to one skilled in the art and it is intended that the invention encompass such changes and modifications as fall within the scope of the appended claims.

I claim:

1. A sterile, aqueous contact lens wetting composition comprising:
   (a) trimethoprim and an adjuvant bactericide comprising benzyl alcohol, present together in an amount for maintaining the sterility of the composition; and
   (b) at least one wetting agent suitable for wetting contact lenses.

2. The wetting composition as recited in claim 1 wherein trimethoprim is present in an amount of from about 0.05% to about 2.0% by weight of the total composition.

3. The wetting composition as recited in claim 1 wherein benzyl alcohol is present in an amount of from about 0.1% to about 5.0% by weight of the total composition.

4. The wetting composition as recited in claim 2 wherein benzyl alcohol is present in an amount of from about 0.1% to about 5.0% by weight of the total composition.

5. The wetting composition as recited in claim 1 further comprising ethylenediaminetetraacetic acid or a water soluble salt thereof present in an amount of from about 0.025% to about 0.5% by weight of the total composition.

6. The wetting composition as recited in claim 5 wherein the disodium salt of ethylenediaminetetraacetic acid is present in said composition.

7. The wetting composition of claim 1 wherein said wetting agent is selected from the group consisting of polyvinyl alcohol, polyvinylpyrrolidone and mixtures thereof.

8. The wetting composition of claim 1 further comprising a water soluble cellulosic polymer viscosity building agent selected from the group consisting of hydroxyethylcellulose, methylcellulose, carboxymethylcellulose, natural gums and mixtures thereof.

9. The wetting composition of claim 1 further comprising a buffer for maintaining the pH of the composition in the range of from about 7.0 to 8.0.

10. The wetting composition of claim 9 wherein said buffer includes sodium bicarbonate, sodium phosphate and sodium bisulfite.

11. The wetting composition of claim 1 wherein the composition has a tonicity in the range of from about 1.00 to 1.45.

12. An aqueous contact lens wetting composition comprising:
   (a) from about 0.01% to about 2.0% trimethoprim by weight of the total composition;
   (b) a first adjuvant bactericide comprising from about 0.1% to about 5.0% benzyl alcohol by weight of the total composition and a second adjuvant bactericide comprising ethylenediaminetetraacetic acid or a water soluble salt thereof present in an amount of from about 0.025% to about 0.5% by weight of the total composition;
   (c) hydroxyethylcellulose present in an amount of from about 0.05% to about 0.80% by weight of the total aqueous composition;
   (d) polyvinyl alcohol present in an amount of from about 0.5% to about 2.5% by weight of the total aqueous composition; and
   (e) polyvinylpyrrolidone present in an amount of from about 0.5% to about 2.0% by weight of the total composition.

13. The composition as recited in claim 12 further comprising a buffer for maintaining the pH of the composition in the range of from about 7.0 to 8.0.

14. The wetting composition as recited in claim 12 wherein said composition has a tonicity of from about 1.26 to about 1.45.

15. The wetting composition as recited in claim 12 wherein trimethoprim is present in an amount of from about 0.01% to about 0.05% by weight of the total composition.

16. The wetting composition as recited in claim 12 wherein the composition contains, by weight of the total composition, about 0.025% trimethoprim, about 0.2% benzyl alcohol, about 0.40% hydroxyethylcellulose, about 1.0% polyvinyl alcohol, about 0.5% polyvinylpyrrolidone and about 0.1% of the disodium salt of ethylenediaminetetraacetic acid and the composition further comprises, by weight of the total composition, about 0.10% sodium bicarbonate, about 0.030% sodium phosphate, about 0.050% sodium bisulfite, about 0.790% sodium chloride, about 0.368% potassium chloride, about 0.030% sodium biphosphate and about 0.50% propylene glycol.

17. A method of maintaining the sterility of an aqueous contact lens wetting composition suitable for use in the eye comprising providing in the composition a preservative system for an aqueous contact lens wetting composition comprising:
   (a) from about 0.05% to about 2.0% trimethoprim by weight of the total wetting composition; and
   (b) a first adjuvant bactericide comprising from about 0.1% to about 5.0% benzyl alcohol by weight of the total wetting composition and a second adjuvant bactericide comprising from about 0.025% to about 0.5% ethylenediaminetetraacetic acid or a water soluble salt thereof by weight of the total composition.

18. The method as recited in claim 17 wherein trimethoprim is present in an amount of from about 0.075% to about 0.3% by weight of the total wetting composition.

19. The method as recited in claim 17 wherein benzyl alcohol is present in an amount of about 0.2% by weight of the total wetting composition.

* * * * *

UNITED STATES PATENT AND TRADEMARK OFFICE
CERTIFICATE OF CORRECTION

PATENT NO. : 4,560,491

DATED : December 24, 1985

INVENTOR(S) : Guy J. Sherman

It is certified that error appears in the above-identified patent and that said Letters Patent is hereby corrected as shown below:

Column 4, line 26, after "suitable" insert --for--.

Column 6, after line 58, insert --An especially preferred wetting composition is:--

Signed and Sealed this

Twenty-ninth Day of April 1986

[SEAL]

Attest:

DONALD J. QUIGG

Attesting Officer

Commissioner of Patents and Trademarks